US008764739B2

(12) United States Patent
Boutoussov et al.

(10) Patent No.: US 8,764,739 B2
(45) Date of Patent: Jul. 1, 2014

(54) SATELLITE-PLATFORMED ELECTROMAGNETIC ENERGY TREATMENT DEVICE

(75) Inventors: Dmitri Boutoussov, Dana Point, CA (US); Mikhail Atlas, Laguna Hills, CA (US)

(73) Assignee: Biolase, Inc., Irvine, CA (US)

( * ) Notice: Subject to any disclaimer, the term of this patent is extended or adjusted under 35 U.S.C. 154(b) by 1000 days.

(21) Appl. No.: 12/579,890

(22) Filed: Oct. 15, 2009

(65) Prior Publication Data

US 2010/0100086 A1    Apr. 22, 2010

Related U.S. Application Data

(63) Continuation-in-part of application No. 11/800,435, filed on May 3, 2007, now Pat. No. 7,815,630, which is a continuation-in-part of application No. 11/698,345, filed on Jan. 25, 2007.

(60) Provisional application No. 61/105,782, filed on Oct. 15, 2008, provisional application No. 60/921,057, filed on Mar. 29, 2007.

(51) Int. Cl.
*A61B 18/18*    (2006.01)

(52) U.S. Cl.
USPC .................................. 606/13; 606/3; 607/88

(58) Field of Classification Search
USPC ............... 607/88–90; 433/25, 29, 49–54, 60; 606/1–3, 8–13, 19
See application file for complete search history.

(56) References Cited

U.S. PATENT DOCUMENTS

| 5,700,259 | A | * | 12/1997 | Negus et al. .................... 606/14 |
| 7,815,630 | B2 | * | 10/2010 | Rizoiu et al. ...................... 606/1 |
| 2004/0073202 | A1 | | 4/2004 | Illich et al. |

(Continued)

FOREIGN PATENT DOCUMENTS

| JP | 10-328199 | 12/1998 |
| JP | 2003-523799 | 8/2003 |

(Continued)

OTHER PUBLICATIONS

Office Action (with English-language translation) of related/corresponding Japanese Patent Application No. Tokugan-2011-532251.

(Continued)

*Primary Examiner* — Ahmed Farah
(74) *Attorney, Agent, or Firm* — Jones Day

(57) ABSTRACT

A satellite platform facilitates the dividing of a laser system into functional modules, and operates to provide one or more of the functional modules directly into (e.g., closer toward) a user's operational space. In a typical implementation, the satellite platform pairs two or more of the functional modules into a combination and places it in the user's operational space. The two or more functional modules can be two of the major components of the laser-system user interface, namely, the handpiece and the control panel. The combination is provided by way of the satellite platform directly into the user's operational space, while part, all, or a majority of, the laser system may remain away from the use's operational space (e.g., on the wall, on the counter-top or at the walk-way). A particular embodiment of the satellite platform takes the form of an articulated arm similar to that used for components in conventional dental chairs.

17 Claims, 1 Drawing Sheet

(56) References Cited

U.S. PATENT DOCUMENTS

2006/0142657 A1   6/2006   Quaid et al.
2008/0077198 A1*  3/2008   Webb et al. .................. 607/88
2008/0219629 A1   9/2008   Rizoiu et al.

FOREIGN PATENT DOCUMENTS

JP       2003-180708     7/2009
JP       2001-245899     9/2011
WO      0149194 A2     7/2001

OTHER PUBLICATIONS

International Search Report and Written Opinion, PCT/US09/60846, mailed Dec. 15, 2009.
Supplementary European Search Report, EP 09821255, mailed Mar. 13, 2012.
Office Action issued on Oct. 16, 2013 in related/corresponding Japanese Patent Application No. 2011-532251, filed Apr. 12, 2011.
Examination Report issued on Aug. 12, 2013 in related/corresponding Australian Patent Appl. No. 2009305681 filed Apr. 8, 2011.

* cited by examiner

US 8,764,739 B2

SATELLITE-PLATFORMED ELECTROMAGNETIC ENERGY TREATMENT DEVICE

CROSS-REFERENCE TO RELATED APPLICATIONS

This application claims the benefit of Prov. App. 61/105,782, filed Oct. 15, 2008 and entitled RE-CONFIGURABLE MODULAR LASER SYSTEM FOR MEDICAL APPLICATIONS, the contents of which are expressly incorporated herein by reference. This application is a continuation-in-part of application Ser. No. 11/800,435, filed May 3, 2007 now U.S. Pat. No. 7,815,630 and entitled TARGET-CLOSE ELECTROMAGNETIC ENERGY EMITTING DEVICE, which claims the benefit of Prov. App. 60/921,057, filed Mar. 29, 2007 and entitled TARGET-CLOSE ELECTROMAGNETIC ENERGY EMITTING DEVICE and which is a continuation-in-part of application Ser. No. 11/698,345, filed Jan. 25, 2007 and entitled ELECTROMAGNETIC ENERGY OUTPUT SYSTEM, the entire contents of all which are hereby incorporated by reference.

BACKGROUND OF THE INVENTION

1. Field of the Invention

The present invention relates generally to medical devices and, more particularly, to energy-outputting tissue treatment devices.

2. Description of Related Art

A variety of laser systems have existed in the prior art. Solid state lasers can be advantageous in that they are compact, reliable for long-term use and easily replaced in the field. A solid-state laser system generally comprises a gain medium (e.g., laser rod) for emitting coherent light and a stimulation source for stimulating the gain medium to emit the coherent light. The gain medium in a solid state laser is a solid material usually having the form of a cylindrical rod. Flashlamps are typically used as stimulation sources, for example, but diodes may be used as well for the excitation source. The use of diodes for generating light amplification by stimulated emission is discussed in the book Solid-State Laser Engineering, Fourth Extensively Revised and Updated Edition, by Walter Koechner, published in 1996, the contents of which are expressly incorporated herein by reference.

A typical conventional laser assembly may comprise a housing containing a laser module, which is connected by way of an optical connector to a trunk fiber. The optical connector can be constructed to facilitate attachment and removal of the trunk fiber to and from the housing, with the trunk fiber extending from the housing up to and through a handpiece. Furthermore, the trunk fiber can continue in an uninterrupted fashion from the handpiece and terminate at an energy output end of the trunk fiber.

SUMMARY OF THE INVENTION

A satellite platform is provided in a laser system for facilitating the parsing or dividing of the laser system into functional modules. According to a feature of the present invention, the satellite platform operates to provide one or more of the modules directly into (e.g., closer toward) a user's operational space.

In a typical implementation, the satellite platform pairs two or more of the functional modules for provision into the user's operational space (e.g., space closest to the user located between the user and a target). An exemplary embodiment includes pairing of two or more of the functional modules (e.g., two of the major components of the laser-system user interface, namely, the handpiece and/or the control panel) into a functional (e.g., separately functional and/or operable or controllable) combination.

The combination is provided by way of the satellite platform directly into the user's operational space, while part, all, or a majority of, the laser system may remain disposed away from the use's operational space (e.g., on a wall, on a countertop or at a walk-way). A particular embodiment of the satellite platform is elucidated in the context of an articulated arm.

While the apparatus and method has or will be described for the sake of grammatical fluidity with functional explanations, it is to be expressly understood that the claims, unless indicated otherwise, are not to be construed as limited in any way by the construction of "means" or "steps" limitations, but are to be accorded the full scope of the meaning and equivalents of the definition provided by the claims under the judicial doctrine of equivalents.

Any feature or combination of features described or referenced herein are included within the scope of the present invention provided that the features included in any such combination are not mutually inconsistent as will be apparent from the context, this specification, and the knowledge of one skilled in the art. In addition, any feature or combination of features described or referenced may be specifically excluded from any embodiment of the present invention. For purposes of summarizing the present invention, certain aspects, advantages and novel features of the present invention are described or referenced. Of course, it is to be understood that not necessarily all such aspects, advantages or features will be embodied in any particular implementation of the present invention. Additional advantages and aspects of the present invention are apparent in the following detailed description and claims that follow.

DETAILED DESCRIPTION OF THE INVENTION

Figure 1:
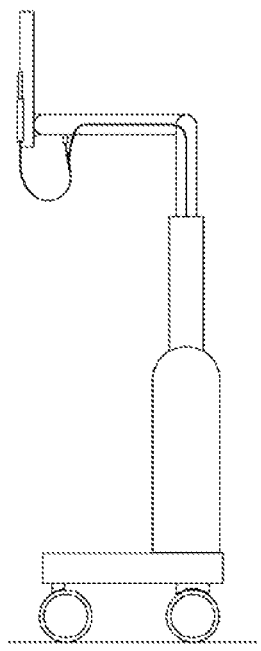
FIG. 1 shows a side elevational view of a modular laser according to a mobile configuration of the present invention.

Embodiments of the invention are now described and illustrated in the accompanying drawings, instances of which are to be interpreted to be to scale in some implementations while in other implementations, for each instance, not. In certain aspects, use of like or the same reference designators in the drawings and description refers to the same, similar or analogous components and/or elements, while according to other implementations the same use should not. According to certain implementations, use of directional terms, such as, top, bottom, left, right, up, down, over, above, below, beneath, rear, and front, are to be construed literally, while in other implementations the same use should not. The present invention may be practiced in conjunction with various devices and techniques that are conventionally used in the art, and only so much of the commonly practiced process steps are included herein as are necessary to provide an understanding of the present invention. The present invention has applicability in the field of laser devices and processes in general. For illustrative purposes, however, the following description pertains to a medical laser device and a method of operating the medical laser device to perform treatments and surgical functions.

The laser system of the present invention can be readily/reversibly (e.g., non-destructibly, without deformation) configured and reconfigured (e.g., within about a minute without the use of tools such as specialized drivers, pliers, drills or cutters), repetitively, an indefinite number of times, for use, interchangeably, as one or more of a stand-alone mobile cabinet, a wall-mounted unit, and a table-top device (e.g., depending on customer preference or particular requirement of a given office or procedure). Attachment or coupling of the laser-system base to a wheeled cart as in FIG. 1, to a wall or pole as in FIG. 2, or to a tabletop as in FIG. 3 can be accomplished using any known structure and technique, or any structure and technique which in light of this disclosure would be apparent, derivable, modifiable, or otherwise recognizable as suitable for achieving such attachment or coupling by one skilled in the relevant art (e.g., of medical devices, lasers, dental instruments, hardware, and/or housings for portable/configurable/detachable devices. Examples of such attachment structures are those commonly referred to as mounts or wall mounts, such as tongue-and-channel mounts which (following an initial setup) do not require bolts or pliers for rapid mounting and un-mounting of the system.

According to a feature of the invention, provided in a laser system is a satellite platform for facilitating the dividing, partitioning or breaking down (i.e., separating) of part or all of the laser system into a plurality of functional modules. The satellite platform separates one or more of the modules from the rest of the laser system and provides the separated one or more modules directly into (e.g., closer to the user than the module or modules would be without the dividing or partitioning) a user's operational space (e.g., space closer or closest to the user and/or located between the user and a target). During performance of a treatment on a target, the user's operational space may be, for instance, the space within an arm's length of the user and/or that located between the user and the target.

In a typical implementation, the satellite platform pairs two or more of the functional modules for provision into, or closer into, the user's operational space. An exemplary embodiment includes pairing of two or more of the functional modules (e.g., two of the major components of the laser-system user interface, namely, the handpiece and the control panel) into a functional (e.g., separately functional) combination.

The combination is provided by way of the satellite platform directly into the user's operational space, while part, all, or a majority of, the laser system may remain away from the use's operational space (e.g., at the walk-way, on the wall, or on the counter-top).

A particular embodiment of the satellite platform is elucidated in the context of an articulated arm, which by way of example and not limitation can be very similar to that used for components with conventional dental chairs.

The laser system can comprise an electromagnetic energy output device suitable for implementing treatment procedures on hard or soft tissue. The electromagnetic energy output device can be configured, for example, to be particularly suited for soft tissue cutting or ablating procedures, and also for decontamination, cleaning periodontal pockets, pain reduction, and biostimulation procedures, to name just an exemplary few.

With reference to the figures, embodiments of the current invention can comprise an electromagnetic energy output device having a system, such as a diode laser system.

Figure 2:
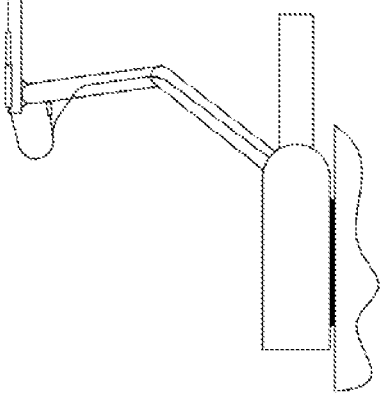
FIG. 2 shows a side elevational view of a modular laser according to a wall-mounted configuration of the present invention.

The electromagnetic energy output device is provided in a modular form with a satellite platform and a base. The base end of the device can be provided in a mobile form such as on wheels as shown in FIG. 1, can be wall or pole mounted as shown in FIG. 2, or can be positioned on a table top as elucidated, for example, in FIG. 3. A housing and/or user-interface part of the device can comprise, for example, a display, such as a touchscreen, inputs and/or controls, and an electromagnetic energy source such as a laser.

According to an aspect of the present invention, part or all of the electromagnetic energy output device is embodied as a target-close electromagnetic energy emitting (e.g., lasing) device. An aspect of the present invention comprises moving forward, along a line of delivery system component locations, components of the target-close functional component. More particularly, one or more of the target-close functional components can be (e.g., are) configured to be positioned more forwardly so that they are disposed closer to the target, as compared to locations of components of typical prior-art systems. In other words, a substantial number of the elements of the target-close functional component, and in certain implementations all of the elements of the device, according to certain aspects of the present invention, be operatively disposed in a relatively close proximity to the target. While referenced herein as a functional component, it is intended that the energy source be interpreted to cover electromagnetic energy sources in general rather than just laser systems.

One feature of the present invention provides for the coupling of a target-close functional component to a satellite platform. Horizontal surface real-estate can be at a premium during lasing procedures, so that movement (and subsequent repositioning) of the target-close functional component from proximity of such surfaces can free-up the surfaces for other tools or uses. One or more components of the target-close functional component may be, for example, mounted to or disposed on (as distinguished from just being coupled) the satellite platform. The one or more components of the target-close functional component may be mounted to or disposed on the satellite platform using one or more of fasteners, such as screws, clips, or straps, and/or gravity/friction. In certain embodiments, the one or more components, and in some implementations, all of the components, of the target-close functional component can be attached to a satellite platform of one or more of an operating table, an operating stand, an operating chair, and a wall.

Another feature of the present invention provides for the coupling of a target-close functional component to a satellite platform, which may comprise but is not limited to any one or more, in any permutation/combination, of the following items, none of which is to be considered equivalent, interchangeable or suggestive of the other: cable (e.g., vertically extending from a ceiling or other relatively high location), wire, bracket, articulated arm, telescoping link and pedestal. The satellite platform is embodied in the illustrated embodiment as an articulated arm.

When attached to a satellite platform (e.g., articulated arm), the target-close functional component does not, in certain implementations, require a surface or mount for placement on a counter or mounting on a wall. Accordingly, horizontal surfaces are conserved. Attachment of the target-close functional component can attenuate a number or length of required cables and/or other conduits, a fatigue of the user, an apprehension of a patient, an amount of clutter in a procedural area, and an amount of set-up time and/or clean-up time of a procedure.

One or more components of the target-close functional component may be mounted to or disposed on (as distinguished from just being coupled) the satellite platform (e.g., articulated arm). The one or more components of the target-close functional component may be mounted to or disposed on the satellite platform (e.g., articulated arm) with one or more of fasteners, such as clips, bands, snaps, grooves, pockets, cases, rings, hook and loop fasteners, mounts, or straps. Moreover, as compared to a conventional disposition of a functional component on a horizontal support surface, it has been discovered that, in the context of coupling of the target-close functional component to the mentioned satellite platform (e.g., articulated arm), the of a user interface with fewer hard (physical) buttons and/or more of a display/software user interface (e.g., comprising more soft key and/or touch screen inputs, as compared to prior-art constructions) can facilitate a greater usability or versatility of the target-close functional component due to, for example, the less-restricting physical nature of the coupling. Similarly, as compared to a conventional functional component, the coupling of the target-close functional component to the mentioned satellite platform (e.g., articulated arm) can provide greater operability and efficiency when implemented with shorter cables and/or conduits/fibers.

A possible net result of the current invention's implementation of a target-close lasing system can be to at least partially, and in certain aspects, dramatically, enhance one or more of a safety (e.g., from a simpler assembly, less clutter on floor/table surfaces and/or less likelihood of user confusion/error), a versatility (e.g., movement/maneuverability of the device to/in or use of the device in more applications), and an efficiency (e.g., shorter fiber optic, less assembly/disassembly). Placement within/on the satellite platform (e.g., articulated arm) of certain functional components, such as laser modules, heat exchanging modules, etc., can reduce a length of the laser power delivery system and/or make better use of the available space. That is, the arm can be filled with functional components, an example being forming the laser in arm right behind the display to reduce the fiber length &/or make the fiber thinner or more flexible. In a further instance, a module that cools the laser can be positioned next to the laser. In yet a further instance, a length and design of the arm can be used for cooling of fluid. Such features can also make the overall system, or parts thereof, lighter and smaller.

Thus, the invention contemplates various approaches for forming the laser and/or its related sub-systems to be modular, functionally configurable and/or re-configurable according, for example, to current customer demand and a state of or specified technology from the manufacturer and/or other party. When the satellite platform is sold or licensed, it can be configurable according to customer requests (ex., an arm may include one, two or three lasers; and/or may include one, two, or three modules and/or a power supply can be a certain dimension according to cost with smaller being more expensive wherein, for example, a base unit may contain a housing (e.g., rectangular) that is 3" deep housing as measured (extending) from the wall (left-to-right dimension in FIG. 2), 10" wide and 20" high. The depth can be the most critical dimension, allowing the entire assembly to rest or form and fit closely to the wall and not intrude into a working space. In the prior-art there tended not to be space in a typical dental office, for example, for a laser, and there tended to be large set-up time requirements for the laser—the present architectures of the invention address both by providing a space-conserving and time-saving (e.g., rapidly configurable) laser system.

Another possible net result of the implementation of a target-close lasing system according to the present invention can be to attenuate at least partially, and in certain aspects, dramatically, one or more of a manufacturing cost (e.g., from more compact, fewer or shorter components), an operational and/or maintenance cost (e.g., from delivery of energy over a smaller distance, resulting in fewer energy loses during use), and a subjective element experienced by the patient during a medical procedure (e.g., from more discrete and/or less formidable-looking equipment, as compared to typical prior-art systems). A typical power output may comprise, for example, 0.5 W to about 2.0 W, or more.

Any combination or permutation of components, systems and steps of or in connection with any target-close functional component described or referenced herein can be used or implemented, to any extent and in any combination or permutation, with any one or more of the components, systems and steps disclosed or referenced in application Ser. No. 11/330,388, filed Jan. 10, 2006, the entire contents of which are expressly incorporated herein by reference. For example, fluid (e.g., atomized fluid particles) can be placed into an interaction zone in front of, for example, any of the output configurations disclosed herein for absorption of electromagnetic radiation and for subsequent expansion to impart an effect (e.g., mechanical cutting forces) onto a target.

Moreover, any one or more of the described or referenced fiber optic tip and distal end of a fiber optic may be provided with one or more of an air and a fluid (e.g., water) line as described, for example, in the referenced application Ser. No. 11/330,388. An air and/or fluid (e.g., sterile water) source may be provided in the form of one or more receptacles (e.g., pressurized cartridges) which may be coupled with (e.g., attached to or housed in) one or more of the components described or referenced herein, such as a housing or handpiece.

Any combination or permutation of components, systems and steps of or in connection with any target-close functional component described or referenced herein can be used or implemented, to any extent and in any combination or permutation, with any one or more of the components, systems and steps disclosed or referenced in application Ser. No. 11/475,719, filed Jun. 26, 2006, the entire contents of which are expressly incorporated herein by reference. For example, a visual feedback implement (e.g., camera) can be disposed in proximity to (e.g., on or within and/or at a distal part thereof) one or more of the described or referenced housing, handpiece, fiber optic tip, and distal end of a fiber optic. According to one example, any one or more of the described or referenced handpiece, fiber optic tip and distal end of the fiber optic may be provided with one or more of a water line and a visual feedback implement.

The housing and the output configuration and physically connected via the satellite link. Furthermore, according to another aspect of the present invention, one or more of the housing and the output configuration can be constructed with one or more of an application specific integrated circuit (ASIC) and a microprocessor. The microprocessor or microprocessors may be enabled, for example, for wireless communication of, for example, operating states and configurations of the target-close functional component. The wireless communications may be performed using, for example, Bluetooth® architectures and protocols, and/or the microprocessor or microprocessors may furthermore, or alternatively, be configured to transfer or upload data of, for example, previously acquired or real-time operating information.

Figure 3:
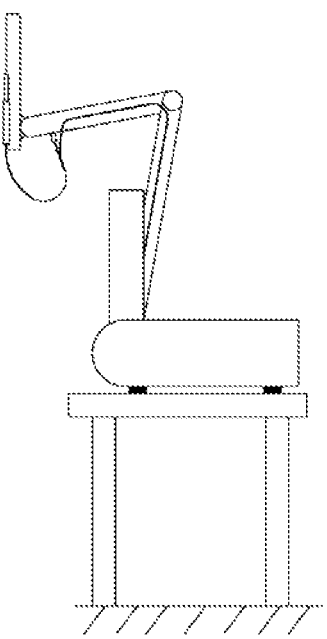
FIG. 3 shows a side elevational view of a modular laser according to a table-top configuration of the present invention.

With regard to FIGS. 1-3, these drawings are intended to be examples of implementations of various aspects of the present invention and are intended, according to certain but not all embodiments, to be to-scale. That is, according to certain implementations, the structures depicted in these figures may be interpreted to be to scale, but in other implementations they may not. In certain aspects of the invention, use of the same reference designator numbers in these drawings and the following description is intended to refer to similar or analogous, but not necessarily the same, components and elements. According to other aspects, use of the same reference designator numbers in these drawings and the following description is intended to be interpreted as referring to the same or substantially the same, and/or functionally the same, components and elements.

In certain constructions of target-close functional components, for example, fiber optic tips, according to one feature of the present invention, can be formed (e.g., of solid glass) with radiation output orifices of 3-10 mm corresponding, for example, to photobiomodulation or low-level light therapy (LLLT) embodiments. Regarding low-level light therapy techniques, any combination or permutation of components, systems and steps of or in connection with any target-close functional component described or referenced herein can be used or implemented, to any extent and in any combination or permutation, with any one or more of the components, systems and steps disclosed or referenced in application Ser. No. 11/447,605, filed Jun. 5, 2006, the entire contents of which are expressly incorporated herein by reference.

According to certain implementations, laser energy generated by the modular laser is output from a power or treatment fiber, and is directed, for example, into fluid (e.g., an air and/or water spray or an atomized distribution of fluid particles from a water connection and/or a spray connection near an output end of the handpiece) that is emitted from a fluid output of a handpiece above a target surface (e.g., one or more of tooth, bone, cartilage and soft tissue). The fluid output may comprise a plurality of fluid outputs, concentrically arranged around a power fiber, as described in, for example, application Ser. No. 11/042,824 and Prov. App. 60/601,415. The power or treatment fiber may be coupled to an electromagnetic energy source comprising one or more of a wavelength within a range from about 2.69 to about 2.80 microns and a wavelength of about 2.94 microns. In certain implementations the power fiber may be coupled to one or more of an Er:YAG laser, an Er:YSGG laser, an Er, Cr:YSGG laser and a CTE:YAG laser, and in particular instances may be coupled to one of an Er, Cr:YSGG solid state laser having a wavelength of about 2.789 microns and an Er:YAG solid state laser having a wavelength of about 2.940 microns. An apparatus including corresponding structure for directing electromagnetic energy into an atomized distribution of fluid particles above a target surface is disclosed, for example, in the below-referenced U.S. Pat. No. 5,574,247, which describes the impartation of laser energy into fluid particles to thereby apply disruptive forces to the target surface.

By way of the disclosure herein, a laser has been described that can output electromagnetic energy useful to diagnose, monitor and/or affect a target surface. In the case of procedures using fiber optic tip energy, a probe can include one or more power or treatment fibers for transmitting treatment energy to a target surface for treating (e.g., ablating) a dental structure, such as within a canal. In any of the embodiments described herein, the light for illumination and/or diagnostics may be transmitted simultaneously with, or intermittently with or separate from, transmission of the treatment energy and/or of the fluid from the fluid output or outputs.

Corresponding or related structure and methods described in the following patents assigned to Biolase Technology, Inc., are incorporated herein by reference in their entireties, wherein such incorporation includes corresponding or related structure (and modifications thereof) in the following patents which may be, in whole or in part, (i) operable with, (ii) modified by one skilled in the art to be operable with, and/or (iii) implemented/used with or in combination with, any part(s) of the present invention according to this disclosure, that of the patents or below applications, and the knowledge and judgment of one skilled in the art.

Such patents include, but are not limited to U.S. Pat. No. 7,578,622 entitled Contra-angle rotating handpiece having tactile-feedback tip ferrule; U.S. Pat. No. 7,575,381 entitled Fiber tip detector apparatus and related methods; U.S. Pat. No. 7,563,226 entitled Handpieces having illumination and laser outputs; U.S. Pat. No. 7,467,946 entitled Electromagnetic radiation emitting toothbrush and dentifrice system; U.S. Pat. No. 7,461,982 entitled Contra-angle rotating handpiece having tactile-feedback tip ferrule; U.S. Pat. No. 7,461,658 entitled Methods for treating eye conditions; U.S. Pat. No. 7,458,380 entitled Methods for treating eye conditions; U.S. Pat. No. 7,424,199 entitled Fiber tip fluid output device; U.S. Pat. No. 7,421,186 entitled Modified-output fiber optic tips; U.S. Pat. No. 7,415,050 entitled Electromagnetic energy distributions for electromagnetically induced mechanical cutting; U.S. Pat. No. 7,384,419 entitled Tapered fused waveguide for delivering treatment electromagnetic radiation toward a target surface; U.S. Pat. No. 7,356,208 entitled Fiber detector apparatus and related methods; U.S. Pat. No. 7,320,594 entitled Fluid and laser system; U.S. Pat. No. 7,303,397 entitled Caries detection using timing differentials between excitation and return pulses; U.S. Pat. No. 7,292,759 entitled Contra-angle rotating handpiece having tactile-feedback tip ferrule; U.S. Pat. No. 7,290,940 entitled Fiber tip detector apparatus and related methods; U.S. Pat. No. 7,288,086 entitled High-efficiency, side-pumped diode laser system; U.S. Pat. No. 7,270,657 entitled Radiation emitting apparatus with spatially controllable output energy distributions; U.S. Pat. No. 7,261,558 entitled Electromagnetic radiation emitting toothbrush and dentifrice system; U.S. Pat. No. 7,194,180 entitled Fiber detector apparatus and related methods; U.S. Pat. No. 7,187,822 entitled Fiber tip fluid output device; U.S. Pat. No. 7,144,249 entitled Device for dental care and whitening; U.S. Pat. No. 7,108,693 entitled Electromagnetic energy distributions for electromagnetically induced mechanical cutting; U.S. Pat. No. 7,068,912 entitled Fiber detector apparatus and related methods; U.S. Pat. No. 6,942,658 entitled Radiation emitting apparatus with spatially controllable output energy distributions; U.S. Pat. No. 6,829,427 entitled Fiber detector apparatus and related methods; U.S. Pat. No. 6,821,272 entitled Electromagnetic energy distributions for electromagnetically induced cutting; U.S. Pat. No. 6,744,790 entitled Device for reduction of thermal lensing; U.S. Pat. No. 6,669,685 entitled Tissue remover and method; U.S. Pat. No. 6,616,451 entitled Electromagnetic radiation emitting toothbrush and dentifrice system; U.S. Pat. No. 6,616,447 entitled Device for dental care and whitening; U.S. Pat. No. 6,610,053 entitled Methods of using atomized particles for electromagnetically induced cutting; U.S. Pat. No. 6,567,582 entitled Fiber tip fluid output device; U.S. Pat. No. 6,561,803 entitled Fluid conditioning system; U.S. Pat. No. 6,544,256 entitled Electromagnetically induced cutting with atomized fluid particles for dermatological applications; U.S. Pat. No. 6,533,775 entitled Light-activated hair treatment and removal device; U.S. Pat. No. 6,389,193 entitled Rotating handpiece; U.S. Pat. No. 6,350,123 entitled Fluid conditioning system; U.S. Pat. No. 6,288,499 entitled Electromagnetic energy distributions for electromagnetically induced mechanical cutting; U.S. Pat. No. 6,254,597 entitled Tissue remover and method; U.S. Pat. No. 6,231,567 entitled Material remover and method; U.S. Pat. No. 6,086,367 entitled Dental and medical procedures employing laser radiation;

U.S. Pat. No. 5,968,037 entitled User programmable combination of atomized particles for electromagnetically induced cutting; U.S. Pat. No. 5,785,521 entitled Fluid conditioning system; and U.S. Pat. No. 5,741,247 entitled Atomized fluid particles for electromagnetically induced cutting.

Also, the above disclosure and referenced items, and that described on the referenced pages, are intended to be operable or modifiable to be operable, in whole or in part, with corresponding or related structure and methods, in whole or in part, described in the following published applications and items referenced therein, which applications are listed as follows: App. Pub. 20090035717 entitled Electromagnetic radiation emitting toothbrush and transparent dentifrice system; App. Pub. 20090031515 entitled Transparent dentifrice for use with electromagnetic radiation emitting toothbrush system; App. Pub. 20080276192 entitled Method and apparatus for controlling an electromagnetic energy output system; App. Pub. 20080240172 entitled Radiation emitting apparatus with spatially controllable output energy distributions; App. Pub. 20080221558 entitled MULTIPLE FIBER-TYPE TISSUE TREATMENT DEVICE AND RELATED METHOD; App. Pub. 20080212624 entitled DUAL PULSE-WIDTH MEDICAL LASER; App. Pub. 20080157690 entitled Electromagnetic energy distributions for electromagnetically induced mechanical cutting; App. Pub. 20080151953 entitled Electromagnet energy distributions for electromagnetically induced mechanical cutting; App. Pub. 20080125677 entitled Methods for treating hyperopia and presbyopia via laser tunneling; App. Pub. 20080125676 entitled Methods for treating hyperopia and presbyopia via laser tunneling; App. Pub. 20080097418 entitled Methods for treating eye conditions; App. Pub. 20080097417 entitled Methods for treating eye conditions; App. Pub. 20080097416 entitled Methods for treating eye conditions; App. Pub. 20080070185 entitled Caries detection using timing differentials between excitation and return pulses; App. Pub. 20080065057 entitled High-efficiency, side-pumped diode laser system; App. Pub. 20080065055 entitled Methods for treating eye conditions; App. Pub. 20080065054 entitled Methods for treating hyperopia and presbyopia via laser tunneling; App. Pub. 20080065053 entitled Methods for treating eye conditions; App. Pub. 20080033411 entitled High efficiency electromagnetic laser energy cutting device; App. Pub. 20080033409 entitled Methods for treating eye conditions; App. Pub. 20080033407 entitled Methods for treating eye conditions; App. Pub. 20080025675 entitled Fiber tip detector apparatus and related methods; App. Pub. 20080025672 entitled Contra-angle rotating handpiece having tactile-feedback tip ferrule; App. Pub. 20080025671 entitled Contra-angle rotating handpiece having tactile-feedback tip ferrule; App. Pub. 20070298369 entitled Electromagnetic radiation emitting toothbrush and dentifrice system; App. Pub. 20070263975 entitled Modified-output fiber optic tips; App. Pub. 20070258693 entitled Fiber detector apparatus and related methods; App. Pub. 20070208404 entitled Tissue treatment device and method; App. Pub. 20070208328 entitled Contra-angel rotating handpiece having tactile-feedback tip ferrule; App. Pub. 20070190482 entitled Fluid conditioning system; App. Pub. 20070184402 entitled Caries detection using real-time imaging and multiple excitation frequencies; App. Pub. 20070104419 entitled Fiber tip fluid output device; App. Pub. 20070060917 entitled High-efficiency, side-pumped diode laser system; App. Pub. 20070059660 entitled Device for dental care and whitening; App. Pub. 20070054236 entitled Device for dental care and whitening; App. Pub. 20070054235 entitled Device for dental care and whitening; App. Pub. 20070054233 entitled Device for dental and whitening; App. Pub. 20070042315 entitled Visual feedback implements for electromagnetic energy output devices; App. Pub. 20070014517 entitled Electromagnetic energy emitting device with increased spot size; App. Pub. 20070014322 entitled Electromagnetic energy distributions for electromagnetically induced mechanical cutting; App. Pub. 20070009856 entitled Device having activated textured surfaces for treating oral tissue; App. Pub. 20070003604 entitled Tissue coverings bearing customized tissue images; App. Pub. 20060281042 entitled Electromagnetic radiation emitting toothbrush and dentifrice system; App. Pub. 20060275016 entitled Contra-angle rotating handpiece having tactile-feedback tip ferrule; App. Pub. 20060241574 entitled Electromagnetic energy distributions for electromagnetically induced disruptive cutting; App. Pub. 20060240381 entitled Fluid conditioning system; App. Pub. 20060210228 entitled Fiber detector apparatus and related methods; App. Pub. 20060204203 entitled Radiation emitting apparatus with spatially controllable output energy distributions; App. Pub. 20060142743 entitled Medical laser having controlled-temperature and sterilized fluid output; App. Pub. 20060099548 entitled Caries detection using timing differentials between excitation and return pulses; App. Pub. 20060043903 entitled Electromagnetic energy distributions for electromagnetically induced mechanical cutting; App. Pub. 20050283143 entitled Tissue remover and method; App. Pub. 20050281887 entitled Fluid conditioning system; App. Pub. 20050281530 entitled Modified-output fiber optic tips; App. Pub. 20040106082 entitled Device for dental care and whitening; App. Pub. 20040092925 entitled Methods of using atomized particles for electromagnetically induced cutting; App. Pub. 20040091834 entitled Electromagnetic radiation emitting toothbrush and dentifrice system; App. Pub. 20040068256 entitled Tissue remover and method; App. Pub. 20030228094 entitled Fiber tip fluid output device; App. Pub. 20020149324 entitled Electromagnetic energy distributions for electromagnetically induced mechanical cutting; and App. Pub. 20020014855 entitled Electromagnetic energy distributions for electromagnetically induced mechanical cutting.

All of the contents of the preceding published applications are incorporated herein by reference in their entireties. Although the disclosure herein refers to certain illustrated embodiments, it is to be understood that these embodiments have been presented by way of example rather than limitation. For example, any of the energy outputs (e.g., lasers), any of the fluid outputs (e.g., water outputs), and any conditioning agents, particles, agents, etc., and particulars or features thereof, or other features, including method steps and techniques, may be used with any other structure(s) and process described or referenced herein, in whole or in part, in any combination or permutation as a non-equivalent, separate, non-interchangeable aspect of this invention. Corresponding or related structure and methods specifically contemplated, disclosed and claimed herein as part of this invention, to the extent not mutually inconsistent as will be apparent from the context, this specification, and the knowledge of one skilled in the art, including, modifications thereto, which may be, in whole or in part, (i) operable and/or constructed with, (ii) modified by one skilled in the art to be operable and/or constructed with, and/or (iii) implemented/made/used with or in combination with, any parts of the present invention according to this disclosure, include: (I) any one or more parts of the above disclosed or referenced structure and methods and/or (II) subject matter of any one or more of the following claims and parts thereof, in any permutation and/or combination. The intent accompanying this disclosure is to have such embodiments construed in conjunction with the knowledge of one skilled in the art to cover all modifications, variations, combinations, permutations, omissions, substitutions, alternatives, and equivalents of the embodiments, to the extent not mutually exclusive, as may fall within the spirit and scope of the invention as limited only by the appended claims.

What is claimed is:

1. An apparatus comprising:
a satellite platform;
an output configuration coupled to the satellite platform and formed as a handpiece, an electromagnetic energy source actuable by a user to output electromagnetic energy, a first circuit, a data transmitter and receiver, and a sterile output end constructed to deliver ablating or therapeutic energy from the electromagnetic, energy source to a target; and
a housing including, a second circuit, a graphical user interface having a display and one or more of user inputs and user controls, and a data transmitter and receiver that is configured to communicate one or more of operating states, configurations and real-time operating information with the first circuit;
wherein the output configuration is hard-wire and physically connected to the housing; and
the apparatus further comprises a wireless communication link between the housing and at least one of the satellite platform and the handpiece.

2. The apparatus as set forth in claim 1, wherein the energy is pulsed and the satellite platform is an articulated item.

3. The apparatus as set forth in claim 1, wherein the satellite platform is an articulated arm and the output configuration comprises an outer surface sized and shaped to facilitate one or more of holding and gripping by a hand of a user.

4. The apparatus as set forth in claim 1, wherein the output configuration is hard-wire and physically connected to the housing and the satellite platform is an articulated arm.

5. The apparatus as set forth in claim 1, wherein the satellite platform is an articulated arm and the output configuration comprises a laser having one of a wavelength within a range from about 2.69 to about 2.80 microns and a wavelength of about 2.94 microns.

6. The apparatus as set forth in claim 1, wherein:
the electromagnetic energy is generated by one or more of an Er:YAG, an Er:YSGG, an Er, Cr:YSGG and a CTE:YAG laser; and
the apparatus is operable to ablate or cut one or more of tooth, bone, cartilage and soft tissue.

7. The apparatus as set forth in claim 1, wherein:
the apparatus is configured to output pulsed laser energy;
the output configuration comprises a touchscreen display; and
the output configuration comprises a fluid output configured to deliver fluid from a distal end of the output configuration.

8. The apparatus as set forth in claim 1 wherein the satellite platform is an articulated arm.

9. An apparatus comprising;
a satellite platform;
an output configuration coupled to the satellite platform and formed as a handpiece, an electromagnetic energy source actuable by a user to output electromagnetic energy, a first circuit, a data transmitter and receiver, and a sterile output end constructed to deliver ablating or therapeutic energy from the electromagnetic energy source to a target; and
a housing including, a second circuit, a graphical user interface having a display and one or more of user inputs and user controls, and a data transmitter and receiver that is configured to communicate one or more of operating states, configurations and real-time operating information with the first circuit;
wherein:
the apparatus is operable to output, simultaneously with the electromagnetic energy, fluid particles comprising water; and
the apparatus comprises an atomizer and is configured to place atomized fluid particles into a volume along with electromagnetic energy whereby energy is imparted into the atomized fluid particles in the volume to thereby explosively expand the atomized fluid particles.

10. An apparatus comprising:
a satellite platform including a handpiece actuatable by a user to output electromagnetic energy, and a graphical user interface having a display and one or more of user inputs and user controls; and
a housing including a laser, a power supply, and a circuit configured to communicate one or more of operating states, configurations and real-time operating information with the satellite platform;
wherein the satellite platform is hard-wired and physically connected to the housing; and
the apparatus further comprises a wireless communication link between the housing and at least one of the satellite platform and the handpiece.

11. The apparatus as set forth in claim 10, wherein the energy is pulsed and the satellite platform is an articulated arm.

12. The apparatus as set forth in claim 10, wherein the satellite platform is an articulated arm and the handpiece comprises an outer surface sized and shaped to facilitate one or more of holding and gripping by a hand of a user.

13. The apparatus as set forth in claim 10, Wherein the handpiece is hard-wire and physically connected to the housing and the satellite platform is an articulated arm.

14. The apparatus as set forth in claim 10, wherein the wireless communication link is between the satellite platform and the housing.

15. The apparatus as set forth in claim 10, wherein wireless communication link is between the handpiece and the housing.

16. The apparatus as set forth in claim 10, wherein the satellite platform is an articulated arm.

17. The apparatus as set forth in claim 16, wherein the electromagnetic energy comprises one of a wavelength within a range from about 2.69 to about 2.80 microns and a wavelength of about 2.94 microns.

* * * * *